United States Patent [19]

Trenzeluk

[11] Patent Number: 4,857,328

[45] Date of Patent: Aug. 15, 1989

[54] SKIN THERAPEUTIC MIXTURE CONTAINING ALOE VERA EXTRACT

[75] Inventor: Theodore Trenzeluk, Manville, N.J.

[73] Assignee: Tecma Laboratories, Inc., Manville, N.J.

[21] Appl. No.: 912,590

[22] Filed: Sep. 29, 1986

[51] Int. Cl.$^4$ .............. A61K 35/78; A61K 33/30; A61K 31/425; A61K 31/01

[52] U.S. Cl. ............... 424/195.1; 424/145; 424/DIG. 13; 514/370; 514/762; 514/859; 514/863; 514/928

[58] Field of Search ............ 424/195.1, 145, DIG. 13; 514/370, 762, 859, 863, 928

[56] References Cited

U.S. PATENT DOCUMENTS

| | | | |
|---|---|---|---|
| 112,329 | 3/1881 | Field | 424/159 |
| 230,365 | 7/1880 | Watts | 424/195.1 |
| 915,781 | 3/1909 | Marshall | 424/195.1 |
| 1,519,755 | 12/1924 | Chapman | 424/195.1 |
| 1,627,963 | 5/1927 | Fuller | 424/195.1 |
| 2,370,561 | 2/1945 | Mecca | 514/106 |
| 2,843,522 | 7/1958 | Mahon | 424/145 |
| 3,878,197 | 4/1975 | Maret et al. | 424/195.1 |
| 3,892,853 | 7/1975 | Cobble | 424/195.1 |
| 3,920,816 | 11/1975 | Seegall et al. | 514/970 |
| 4,178,372 | 12/1979 | Coats | 424/195.1 |
| 4,215,049 | 7/1980 | Takahashi et al. | 268/343.3 |
| 4,258,035 | 3/1981 | Spies | 424/195.1 |
| 4,302,443 | 11/1981 | De Navarre et al. | 424/68 |
| 4,369,180 | 1/1983 | Mihalovits | 514/2 |
| 4,446,131 | 5/1984 | Maughan | 424/195.1 |
| 4,474,751 | 10/1984 | Haslam et al. | 424/78 |
| 4,505,902 | 3/1985 | Millard | 424/195.1 |
| 4,670,265 | 6/1987 | Sydiskis et al. | 424/195.1 |
| 4,713,242 | 12/1987 | Trenzeluk | |

OTHER PUBLICATIONS

Merck Index, 9th Ed., Nos. 8739 and 9812, 1976.

*Primary Examiner*—John W. Rollins
*Attorney, Agent, or Firm*—R. Martin Oliveras

[57] ABSTRACT

According to the present invention, a skin therapeutic mixture is useful for the alleviation of certain skin disorders such as acne, psoriasis, burns, pimples, blackheads, and open sores, and such mixture comprises: the therapeutic agent being the extract from the dried leaves of the Aloe Vera plant; a preservative chosen from the group consisting of a sulfaderivative such as sulfathiazole and an alcohol amine; a skin softener such as an oil; and an oil soluble base. An inert pigment such as zinc oxide and a fragrance such as a perfume may be added. According to a specific illustrative embodiment of the present invention, the skin therapeutic mixture comprises about 7.4% by weight of the extract from the dried leaves of the Aloe Vera plant as the therapeutic agent; 5% by weight of sulfathiazole as the preservative; about 14.2% by weight of zinc oxide as the inert white pigment; and about 73.4% by weight of petrolatum.

2 Claims, No Drawings

SKIN THERAPEUTIC MIXTURE CONTAINING ALOE VERA EXTRACT

1. Field of the Invention

This invention relates to skin therapeutic preparations and in particular to such preparations which include the extract from the dried leaves of the Aloe Vera plant as the therapeutic agent.

2. Other Related Applications

None.

Discussion Of The Prior Art

Several prior art patents disclose medical or therapeutic mixtures as follows:

Field U.S. Pat. No. 112,329 entitled "Improvement In Medical Compounds For Cure Of Catarrh And Asthma" discloses a solution comprising water, potassium nitrate, potassium chlorate, licorice extract, boneset leaves, hemp leaves, stromonium leaves, cabela leaves, Virginia snake root, and gum myrrh;

Watts U.S. Pat. No. 230,365 entitled "Liniment" discloses a liniment comprises wild cherry, wild thistle, spearmint, coal oil, turpentine, peppermint, bicarbonate of soda, ammonia, and camphor;

Marshall U.S. Pat. No. 915781 entitled "Hair Tonic" discloses a hair tonic consisting of an intimate mixture of olive oil in an aqueous extract of the leaves of elder, crab apple, morning glory, night shade, wild sage, horseradish, boneset, and sheep sorrel;

Chapman U.S. Pat. No. 1,519,755 entitled "Powdered Preparation For Poultices" discloses a poultice preparation composed of a mixture of dry powdered vegetable materials including boneset, sweet fern, and a glutinous material;

Fuller U.S. Pat. No. 1,627,963 entitled "Medicinal Product" discloses a fluid extract and tincture comprising a vegetable drug used as a remedial agent and a halogen containing ester of glycerine;

Mecca U.S. Pat. No. 2,370,561 entitled "Therapeutic Product And Method Of Making Same" discloses a therapeutic product comprising the active molecular structure of allantoin and a sulfa compound;

Mahon U.S. Pat. No. 2,843,522 entitled "Perianal Ointment" discloses a water repellant perianal ointment comprising petrolatum, para di isobutyl cresoxy ethyl di methyl benzyl ammonium chloride, and calcium caseinate;

Maret U.S. Pat. No. 3,878,197 entitled "Processing For Preparing Extracts Of Aloe Vera" discloses the process comprising the steps of cutting the rind and aloins of an aloe vera leaf from the gel, and agitating the gel under ultraviolet radiation in a digestion liquid containing amine, phosphorus ions, and potassium ions at a given pH;

Cobble U.S. Pat. No. 3,892,853 entitled "Stabilized Aloe Vera Gel And Preparation Of Same" discloses the process comprising the steps of mechanical separation, homogenization, addition of hydrogen peroxide, heating to a given temperature, addition of an effective preparation of a nontoxic buffer to maintain a given pH range;

Seegal et al U.S. Pat. No. 3,920,816 entitled "Composition For Treating Respiratory Diseases" discloses a composition consisting of the juice from the freshly cut leaves of the plant aloe arborescens obtained by extracting the leaves in boiling bees honey;

Coats U.S. Pat. No. 4,178,372 entitled "Hypoallergenic Stabilized Aloe Vera Gel" discloses a process comprising the steps of mechanical separation, extrusion, heating to a given temperature range, addition of a catalytic amount of hydrogen peroxide, addition of ascorbic acid, and addition of citric acid to maintain a given pH range;

Takahashi et al U.S. Pat. No. 4,215,049 entitled "Antitumorgenic Lactone Derivative" discloses a hiyodorolacton-B having a given formula;

Spies U.S. Pat. No. 4,258,035 entitled "Method And Compound For Treatment of Arthritic Conditions In Dogs" discloses a mixture of herbal components consisting essentially of camfrey, mullein, fenugeek, nettle, broom tops, and beneset;

De Navarre U.S. Pat. No. 4,302,443 entitled "Non Irritating Anti Perspirant" discloses a composition comprising aluminum chlorohydroxide and an extract of the aloe vera plant;

Mihalovits U.S. Pat. No. 4,369,180 entitled "Cosmetic Facial Preparation Containing Aloe Vera" discloses a preparation comprising aloe vera, citric acid, potassium sorbate, sodium benzoate, cornstarch, albumin, hydroxy propyl methyl cellulose, allantoin, vitamin A, vitamin D2, and vitamin E;

Maughan U.S. Pat. No. 4,446,131 entitled "Controlled Temperature Process For Manufacturing Of Improved Stabilized Aloe Vera" discloses a process comprising the steps of heating to a given temperature range, addition of ascorbic acid, maintaining the mixture within a given temperature range, and cooling to ambient temperature in less than one hour;

Haslam et al U.S. Pat. No. 4,474,751 entitled "Ophthalmic Drug Delivery System Utilizing Thermosetting Gels" discloses an aqueous composition comprising a given polymer by formula, a pharmaceutic or diagnostic agent, and a pharmaceutically acceptable acid or base to adjust the pH within a certain range; and Millard U.S. Pat. No. 4,505,902 entitled "Skin Treatment Preparation" discloses a preparation comprising mineral oil, apricot kernal oil, avocado oil, cod liver oil, propylparaben, and butylated hydroxy anisole.

The above cited prior art patents do not appear to disclose the subject skin therapeutic mixture including the extract from the dried leaves of the Aloe Vera plant as the therapeutic agent.

Objects of the present invention are therefore to provide a skin therapeutic mixture:

for the alleviation of certain skin disorders;
with few known side effects;
that does not irritate the skin;
for treatment of the skin to provide moisture thereto, to promote healing, and to maintain a healthy condition;
for the alleviation of acne, psoriasis, burns, pimples, blackheads, and open sores.

SUMMARY OF THE PRESENT INVENTION

A summary and features of the present invention are therefore that:

a. according to the present invention, a skin therapeutic mixture for alleviation of the aformentioned skin conditions comprises the therapeutic agent being the extract from the dried leaves of the Aloe Vera plant, a preservative chosen from the group consisting of a sulfa derivative such as sulfathiazole and an alcohol amine, a skin softener such as an oil, and an oil soluble base;

b. an inert pigment such as zinc oxide and a fragrance such as a perfume may be added to the mixture;

c. according to a first illustrative embodiment of the present invention, the skin therapeutic mixture comprises the extract from the dried leaves of the Aloe Vera plant as the therapeutic agent, sulfathiazole as the preservative, zinc oxide as a white inert pigment, and petrolatum as the base;

d. according to a second illustrative embodiment of the present invention, the skin therapeutic mixture comprises a water phase, an oil phase, and perfume as the fragrance, said water phase further comprising the extract from the leaves of the Aloe Vera plant, glycerol, sodium lauryl sulfate, tri ethanol amine, and water; and said oil phase further comprising palmitic acid and cetyl alcohol; and e. according to a third illustrative embodiment of the present invention, the skin theraputic mixture comprises a water phase, an oil phase, and perfume as the fragrance, said water phase further comprising the extract from the dried leaves of the Aloe Vera plant, trie ethanol amine, propylene glycol, propyl p-hydroxy benzoate, and water; and said oil phase further comprising stearic acid, cetyl alcohol, glycerol monosterate, and propyl p-hydroxy benzoate.

An advantage of the present invention is that when applied to the skin surface it is also absorbed into the skin and is able to contact the subject lesion.

DETAILED DESCRIPTION

The above and other objects, features, and advantages of the present invention will be better appreciated from a reading of the following detailed description.

According to the present invention, the skin therapeutic mixture comprises the extract from the dried leaves of the Aloe Vera plant, a preservative, and an oil soluble base. The leaves of the Aloe Vera plant are dried under moderate light, under warm temperatures, and with frequent tossing. The dried leaves are then ground to a very small particle size, and thereafter are extracted with water. The smaller the particle size, the more complete will be the extraction.

The following examples are illustrative of suitable skin therapeutic mixtures containing the extract from the dried leaves of the Aloe Vera plant:

EXAMPLE #1

| Component | Percentage By Weight |
| --- | --- |
| Extract from the dried leaves of the Aloe Vera plant | 7.4 |
| Sulfathiazole | 5.0 |
| Zinc oxide | 14.2 |
| Petrolatum | 73.4 |

In this example the extract and the other ingredients may be blended together most efficiently by warming the petrolatum with moderate stirring to a semi-liquid, then adding the zinc oxide, sulfathiazole, and the extract in that order. The mixture should be stirred in this fashion for about 10 minutes to insure uniformity of the product.

EXAMPLE #2

| Component | Percentage By Weight |
| --- | --- |
| A. Water Phase | |
| Extract from the dried leaves of the Aloe Vera plant | 10 |
| Glycerol | 2 |
| Sodium lauryl sulfate | .2 |
| Tri ethanol amine | .8 |
| Water | 83 |
| B. Oil Phase | |
| Palmitic acid | 3 |
| Cetyl alcohol | .5 |
| C. Perfume for fragrance as needed | .5 |

In this example, the water and oil phases are heated separately while stirring at moderate shear speeds to 75 degrees C. Then add the oil phase to the water phase very slowly to insure good dispersion. The smaller the oil stream in the water, the better the dispersion. Fragrance is then added while stirring in small amounts of same as needed.

EXAMPLE #3

| Component | Percentage By Weight |
| --- | --- |
| A. Water phase | |
| Extract from the dried leaves of the Aloe Vera plant | 8.5 |
| Tri ethanol amine | .95 |
| Propylene glycol | 4.8 |
| Propyl p-hydroxy benzoate | .2 |
| Water | 80 |
| B. Oil phase | |
| Stearic acid | 3 |
| Cetyl alcohol | .6 |
| Glycerol monosterate | 1 |
| Propyl p-hydroxy benzoate | .06 |
| C. Perfume for fragrance as needed | |

In this example, heat the water and oil phases separately to 75 degrees C. Then stir the water phase at moderate shear speeds while adding the oil phase slowly to the water phase.

Several formulations according to the present invention have been tested on animals and humans. The mixtures were found to be nontoxic. The mixtures were tried on over 500 patients for several skin conditions such as psoriasis and others.

A practical range for the overall formulation may the following: the extract from the dried leaves of the Aloe Vera plant being 3% to 50% by weight of the formulation; sulfathiazole being 5% to 20% by weight; zinc oxide being 5% to 16% by weight; and petrolatum being 14% to 87% by weight.

The effective range or limits of the extract are chosen for efficacy at the lower end and for suitable external application at the higher end.

While the arrangement according to the present invention has been described in terms of specific illustrative embodiments, it will be apparent to those skilled in the art that many modifications are possible within the spirit and scope of the disclosed principle.

What is claimed is:

1. A mixture for alleviating the skin conditions of acne, psoriasis, burns, pimples, blackheads, and open sores, said mixture comprising:

a. the aqueous extract from the leaves of the aloe vera plant, said aqueous aloe vera extract being prepared as follows: said leaves being dried under moderate light, under warm temperature, and with frequent tossing; then said dried leaves being ground to a very small particle size; and then said ground leaves being extracted with water; said aqueous aloe vera extract comprising about 3% to about 50% by weight of said mixture;

b. a perservative being sulfathiazole, said preservative comprising about 5% to about 20% by weight of said mixture;

c. an inert pigment being zinc oxide, said inert pigment comprising about 5% to about 16% by weight of said mixture; and d. an oil soluble base being petrolatum, said oil soluble base comprising about 14% to about 87% by weight of said mixture.

2. The mixture of claim 1 wherein said aqueous aloe vera extract comprises about 7.4% to about 10% by weight of said mixture.

* * * * *